US008858967B2

(12) United States Patent
Astruc et al.

(10) Patent No.: US 8,858,967 B2
(45) Date of Patent: Oct. 14, 2014

(54) DERMATOLOGICAL CREAM-GELS CONTAINING AVERMECTIN COMPOUNDS

(75) Inventors: Fanny Astruc, Nice (FR); Sandrine Orsoni, Mandelieu (FR); Laurent Fredon, Roquefort les Pins (FR)

(73) Assignee: Galderma S.A., Cham (CH)

( * ) Notice: Subject to any disclaimer, the term of this patent is extended or adjusted under 35 U.S.C. 154(b) by 1109 days.

(21) Appl. No.: 11/522,312

(22) Filed: Sep. 18, 2006

(65) Prior Publication Data

US 2007/0116731 A1  May 24, 2007

Related U.S. Application Data

(63) Continuation of application No. PCT/EP2005/003718, filed on Mar. 17, 2005.

(60) Provisional application No. 60/556,028, filed on Mar. 25, 2004.

(30) Foreign Application Priority Data

Mar. 18, 2004 (FR) ..................................... 04 02798

(51) Int. Cl.
| | | |
|---|---|---|
| *A01N 43/04* | (2006.01) | |
| *A61K 47/34* | (2006.01) | |
| *A61K 9/00* | (2006.01) | |
| *A61K 47/44* | (2006.01) | |
| *A61K 47/06* | (2006.01) | |
| *A61K 47/10* | (2006.01) | |
| *A61K 31/7048* | (2006.01) | |
| *A61K 47/22* | (2006.01) | |
| *A61K 47/14* | (2006.01) | |
| *A61K 47/26* | (2006.01) | |
| *A61K 47/32* | (2006.01) | |

(52) U.S. Cl.
CPC .................. *A61K 47/32* (2013.01); *A61K 47/34* (2013.01); *A61K 9/0014* (2013.01); *A61K 47/44* (2013.01); *A61K 47/06* (2013.01); *A61K 47/10* (2013.01); *A61K 31/7048* (2013.01); *A61K 47/22* (2013.01); *A61K 47/14* (2013.01); *A61K 47/26* (2013.01)
USPC ........................................... 424/401; 514/28

(58) Field of Classification Search
CPC .................................................... A61K 9/0014
USPC ................................................ 424/401; 514/28
See application file for complete search history.

(56) References Cited

U.S. PATENT DOCUMENTS

| | | | | |
|---|---|---|---|---|
| 5,004,598 | A | * | 4/1991 | Lochhead et al. .............. 424/59 |
| 5,928,632 | A | * | 7/1999 | Reusch ..................... 424/78.03 |
| 5,952,372 | A | | 9/1999 | McDaniel |
| 6,133,310 | A | | 10/2000 | Parks |
| 6,228,348 | B1 | * | 5/2001 | Simon et al. .................... 424/59 |
| 6,399,651 | B1 | * | 6/2002 | Parks ............................ 514/453 |
| 6,511,655 | B1 | * | 1/2003 | Muller et al. ................... 424/59 |
| 2004/0185068 | A1 | * | 9/2004 | Yu et al. ........................ 424/401 |
| 2006/0100165 | A1 | | 5/2006 | Manetta et al. |

FOREIGN PATENT DOCUMENTS

| | | |
|---|---|---|
| EP | 0268164 A2 | 5/1988 |
| FR | 2 854 074 A1 | 10/2004 |
| WO | WO 03/032976 A1 | 4/2003 |
| WO | WO 03/032977 A1 | 4/2003 |
| WO | WO 2004/093886 A1 | 11/2004 |

OTHER PUBLICATIONS

Cosmetics (Cosmetic and Toiletry Formulations, vol. 1 (2nd Edition). William Andrew Publishing/Noyes(1989)).*
XP-002287576 http://www.cetaphil.com/product_information/moisturizers.cfm, (Aug. 7, 2004).
English language translation of an Official Action issued on Dec. 6, 2011 by the Japanese Patent Office in corresponding Japanese Patent Application No. 2007-503311.

* cited by examiner

*Primary Examiner* — Jake Vu
(74) *Attorney, Agent, or Firm* — Dentons US LLP

(57) ABSTRACT

Pharmaceutical cream-gel compositions useful for the treatment of a variety of dermatological conditions, disorders and afflictions, in particular of rosacea, contain at least one avermectin compound active principle, and which also contain an oily phase dispersed in an aqueous phase by means of a non-surfactant polymeric emulsifier, the oily phase comprising oils having a melting point below 30° C. and being free of solid fats having a melting point above 30° C., formulated into a physiologically acceptable medium therefor.

28 Claims, No Drawings

DERMATOLOGICAL CREAM-GELS CONTAINING AVERMECTIN COMPOUNDS

CROSS-REFERENCE TO PRIORITY/PCT/PROVISIONAL APPLICATIONS

This application claims priority under 35 U.S.C. §119 of FR 04/02798; filed Mar. 18, 2004; and of Provisional Application No. 60/556,028; filed Mar. 25, 2004; and is a continuation of PCT/EP 2005/003718 filed Mar. 17, 2005 and designating the United States, published in the English language as WO 2005/089806 A1 on Sep. 29, 2005; each hereby expressly incorporated by reference and each assigned to the assignee hereof.

BACKGROUND OF THE INVENTION

1. Technical Field of the Invention

The present invention relates to pharmaceutical compositions based on a compound of the avermectin family, in the form of a cream-gel comprising, formulated into a physiologically acceptable medium, an oily phase dispersed in an aqueous phase by means of a non-surfactant polymeric emulsifier, said oily phase comprising oils having a melting point below 30° C. and being free or devoid of solid fats having a melting point above 30° C.

This invention also relates to a process for preparing such pharmaceutical compositions and to their utilization in the production of pharmaceutical preparations suited for the treatment of dermatological conditions, disorders or afflictions, in particular of rosacea.

2. Description of Background and/or Related and/or Prior Art

Ivermectin is a mixture of two compounds belonging to the avermectin class, 5-O-demethyl-22,23-dihydroavermectin $A_{1a}$ and 5-O-demethyl-22,23-dihydroavermectin $A_{1b}$. They are also known as 22,23-dihydroavermectin $B_{1a}$ and 22,23-dihydroavermectin $B_{1b}$. Ivermectin contains at least 80% of 22,23-dihydroavermectin $B_{1a}$ and less than 20% of 22,23-dihydroavermectin $B_{1b}$. This active agent is part of the avermectin class, a group of macrocyclic lactones produced by the bacterium *Streptomyces avermitilis* (Reynolds J E F (Ed) (1993) Marindale. The extra pharmacopoeia. 29th Edition. Pharmaceutical Press, London). The avermectins include, in particular, ivermectin, invermectin, avermectin, abamectin, doramectin, eprinomectin and selamectin.

Ivermectin is more particularly an anthelmintic. It has already been described in humans in the treatment of river blindness caused by *Onchocerca volvulus*, of gastrointestine strongyloidosis (anguillulosis) (product Stromectol®), and of human scabies (Meinking T L et al., *N. Engl. J. Med.*, 1995 Jul. 6; 333(1):26-30 The treatment of scabies with ivermectin) and also in the treatment of microfilaremia diagnosed or suspected in individuals suffering from lymphatic filariasis due to *Wuchereria bancrofti*.

U.S. Pat. No. 6,133,310 discloses administering ivermectin topically in the form of a lotion consisting of a mixture of ivermectin and water, and also mentions the possibility of a cream consisting, for its part, of a mixture of ivermectin and an excipient such as propylene glycol or sodium lauryl sulfate, but describes no pharmaceutical composition that is industrially acceptable, i.e., having good cosmeticity and a sufficiently long shelf-life (minimum of 2 years).

Dermatological conditions are often associated with increased sensitivity of the skin, particularly in the case of rosacea, which is an inflammatory dermatosis that affects mainly the central part of the face and is characterized, inter alia, by reddening of the face, hot flashes, and facial erythema. This type of pathology requires particularly the use of pharmaceutical formulations that are easy to spread and impart to the user a pleasant feeling of well-being.

Need, therefore, continues to exist for topical pharmaceutical compositions containing at least one compound of the avermectin family, and more particularly ivermectin, which are completely suitable for the pathology and specifically for sensitive skin, which is industrially acceptable, i.e., the formulation of which is physically stable (without phase separation) and chemically stable (without modification of the stability of the active agent), and which optimizes the penetration of ivermectin into the skin.

SUMMARY OF THE INVENTION

Ivermectin-based compositions in the form of cream-gels have now been developed which satisfy the above desiderata, comprising an oily phase dispersed in an aqueous phase by means of a non-surfactant polymeric emulsifier, said oily phase comprising oils having a melting point below 30° C. and being free of solid fats having a melting point above 30° C.

The subject cream-gel formulations are moisturizing emulsions with a non-greasy texture that is very well tolerated and that contain, as emulsifier, a non-surfactant polymer. This formulation also combines the advantages of a gel (ease of application, rapid release of the active agent, freshness on application) with those of a cream (comfort of the skin, no dryness or tightness that is completely unacceptable for sensitive skin) and is particularly suitable for the treatment of rosacea.

DETAILED DESCRIPTION OF BEST MODE AND SPECIFIC/PREFERRED EMBODIMENTS OF THE INVENTION

Conventional emulsions as described in the prior art are virtually homogeneous unstable systems of two immiscible liquids, one of which is dispersed in the other in the form of fine droplets (micelles). This dispersion is stabilized by means of the action of surfactant emulsifiers which modify the structure and the ratio of the forces at the interface, and therefore increase the stability of the dispersion by decreasing the surface tension energy.

Surfactant emulsifiers are amphiphilic compounds that have a hydrophobic portion with affinity for the oil and a hydrophilic portion with affinity for the water, thus creating a link from the two phases. Ionic or nonionic emulsifiers therefore stabilize oil/water emulsions by adsorbing at the interface and forming lamellar layers of liquid crystals.

The emulsifying power of nonionic surfactants is closely linked to the polarity of the molecule. This polarity is defined by the HLB (hydrophilic/lipophilic balance). Conventional emulsions are generally stabilized by a mixture of surfactants, the HLBs of which can be quite different, but the proportion of which in the mixture corresponds to the required HLB of the fatty phase to be emulsified. This type of surfactant emulsifier is often employed at a concentration of from 3 and 7%.

Non-surfactant polymeric emulsifiers such as acrylate/$C_{10-30}$ alkyl acrylate crosspolymers make it possible to prepare virtually homogeneous systems (oily phase dispersed in an aqueous phase) called polymer emulsions. The polymer emulsification is obtained by steric stabilization: the globules of dispersed phase (oil) are surrounded by hydrophilic polymer that is anchored therein by virtue of a grafted hydrophobic chain.

The crystalline phase is absent and this type of emulsifier does not affect the surface tension, unlike surfactant emulsifiers. These non-surfactant polymeric emulsifiers are hydrophilic compounds that are not characterized by an HLB value and do not form micelles. It is in this respect that polymer emulsions are also called "emulsifier-free systems". These emulsifiers are effective from a concentration of 0.1%.

Moreover, the use, in the oily phase, of the composition of liquid oils having a melting point below 30° C. makes it possible to obtain a fluid cream-gel that is light and has a non-greasy texture on application, and facilitates the preparation of the cream-gel, which can also be produced at ambient temperature.

By virtue of its composition, this cream-gel therefore guarantees that the composition is both stable and innocuous. It is easier to spread than a conventional emulsion due to its gelled structure and its "quick-break" effect, and leaves a pleasant feeling of freshness.

The "quick-break" effect, characterized in that the emulsion "breaks" immediately and releases the aqueous and oily phases, is due to the sensitivity of acrylic acid homopolymers and copolymers to electrolytes. When an emulsion containing this type of polymeric emulsifier is applied to the skin, the polymers come into contact with the salts present thereon. This "quick-break" effect promotes faster release of the phase containing the active agent.

Therefore, it has now surprisingly been determined that the cream-gel compositions according to the invention also allow better release of the bioactive principle and better penetration thereof into the skin, compared with the conventional emulsions.

The present invention therefore features pharmaceutical compositions based on a compound of the avermectin family, in the form of a cream-gel comprising, formulated into a physiologically acceptable medium, an oily phase dispersed in an aqueous phase by means of a non-surfactant polymeric emulsifier, said oily phase comprising oils having a melting point below 30° C. and being free of solid fats having a melting point above 30° C.

The compounds of the avermectin family are selected from among ivermectin, invermectin, avermectin, abamectin, doramectin, eprinomectin and selamectin, and preferably ivermectin.

This invention also features ivermectin-based pharmaceutical compositions in the form of a cream-gel comprising, formulated into a physiologically acceptable medium, an oily phase dispersed in an aqueous phase by means of a non-surfactant polymeric emulsifier, said oily phase comprising oils having a melting point below 30° C. and being free of solid fats having a melting point above 30° C.

The present invention is applicable to any active agent selected from the avermectin family, and in particular avermectin, abamectin, doramectin, eprinomectin and selamectin, and mixtures thereof.

The term "physiologically acceptable medium" means a medium that is compatible with the skin, the mucous membranes, the lips, the nails, the scalp and/or the hair.

The expression "oils having a melting point below 30° C." means oils that are in the liquid state at ambient temperature.

The term "solid fats" means in particular waxes, fatty acids and fatty alcohols having a melting point above 30° C., that are in the solid state at ambient temperature.

The term "free of solid fats" according to the invention means a composition comprising less than 1% of solid fats, preferably less than 0.1%, even more preferably less than 0.05% of solid fats.

The compositions according to the invention are stable emulsions in they have good physical and chemical stability over time, even at a temperature above ambient temperature (for example 45-55° C.), as demonstrated by the examples described below.

The compositions according to the invention are advantageously cream-gels which comprise:
a) an oily phase comprising oils having a melting point below 30° C. and being free of solid fats having a melting point above 30° C.,
b) a non-surfactant polymeric emulsifier,
c) at least one compound of the avermectin family,
d) a solvent and/or a propenetrating agent for the active agent, and
e) water.

The compositions according to the invention are preferably cream-gels which comprise:
a) an oily phase comprising oils having a melting point below 30° C. and being free of solid fats having a melting point above 30° C.,
b) a non-surfactant polymeric emulsifier,
c) ivermectin,
d) a solvent and/or propenetrating agent for the active agent, and
e) water.

The oily phase therefore comprises liquid oils, among which are included, for example, of plant, mineral, animal or synthetic oils, silicone oils, Guerbet alcohols, and mixtures thereof; an apolar mineral oil (high surface tension) of the paraffin oil type will preferably be used.

As examples of mineral oils, representative are, Primol 352; Marcol 82 and Marcol 152; marketed by Esso.

As a plant oil, representative are sweet almond oil, palm oil, soybean oil, sesame oil, sunflower oil, an ester such as cetaryl isononanoate, for instance the product marketed under the trademark Cetiol SN by Cognis France, diisopropyl adipate, for instance the product marketed under the trademark Ceraphyl 230 by ISF, isopropyl palmitate, for instance the product marketed under the trademark Crodamol IPP by Croda, or caprylic/capric triglyceride such as Miglyol 812 marketed by Huls/Lambert Riviere.

As a silicone oil, representative are a dimethicone, for instance the product marketed under the trademark Dow Corning 200 fluid, or a cyclomethicone, for instance the product marketed under the trademark Dow Corning 244 fluid by Dow Corning or the product marketed under the trademark Mirasil CM5 by SACI-CFPA.

The amount of oily phase present in the composition generally ranges from 4 to 60%, and preferably from 5 to 20%, and more precisely from 8 to 12%, by weight relative to the total weight of the composition.

According to the invention, the term "non-surfactant polymeric emulsifier" means an emulsifier system comprising at least one copolymer comprising a major fraction of monomer of mono-olefinically unsaturated $C_3$-$C_6$ carboxylic acid or of its anhydride, and of a minor fraction of monomer of acrylic acid ester containing a fatty chain.

The emulsifying copolymers of the invention are described in EP-A-0-2,681,64 and are obtained according to the preparation methods described therein.

Use is more particularly made of the acrylate/$C_{10}$-$C_{30}$ alkyl acrylate copolymer, such as the products marketed under the trademarks PEMULEN TR 1 and PEMULEN TR 2 or the product marketed under the trademark CARBOPOL 1342 and CARBOPOL 1382 by Goodrich, or else mixtures thereof.

Preferably, the compositions according to the invention comprise a non-surfactant polymeric emulsifier selected from PEMULEN TR1 and PEMULEN TR2.

The amount of non-surfactant polymeric emulsifiers in the compositions according to the invention is generally from 0.25% to 2%, preferably from 0.25 to 1%, and even more preferably from 0.3 to 0.6%, by weight relative to the total weight of the composition.

The compositions according to the invention contain from 0.001 to 10% of ivermectin by weight relative to the total weight of the composition. Preferably, the composition comprises from 0.01 to 5% by weight relative to the total weight of the composition, even more preferably from 0.01 to 1% by weight relative to the total weight of the composition.

By way of example of a solvent and/or a propenetrating agent for the ivermectin active agent, representative are propylene glycol, alcohols such as ethanol, isopropanol, butanol, benzyl alcohol, N-methyl-2-pyrrolidone or DMSO, polysorbate 80; phenoxyethanol, and mixtures thereof.

| Solvents | Maximum % solubility of ivermectin in the solvent under consideration (weight/weight) |
| --- | --- |
| N-methyl-2-pyrrolidone | 58.13 |
| Propylene glycol/oleic acid (4 parts/2 parts) | 27.31 |
| Propylene glycol/polysorbate 80/ phenoxyethanol (4 parts/1 part/1 part) | 28.63 |

The compositions of the invention contain from 0.1% to 20%, and preferably from 1% to 10%, of a solvent and/or a propenetrating agent for the ivermectin active agent.

The compositions of the invention also contain water ranging from 30 to 95%, and preferably from 60 to 80%, by weight relative to the total weight of the composition. The water used in the composition according to the invention will preferably be purified water.

The compositions according to the invention may also comprise a carbomer ranging from 0 to 2%. Among the carbomers, non-limiting examples thereof include CARBOPOL 981, CARBOPOL ETD 2020, CARBOPOL 980 or CARBOPOL Ultrez 10 NF, marketed by BF Goodrich.

The compositions according to the invention may also comprise co-emulsifiers in order to decrease the size of the oily globules of the emulsion formed by the polymeric emulsifier. Exemplary are nonionic surfactants such as Eumulgin B2 (ceteareth 20) or Tween 80 (polysorbate 80) or else sorbitan esters (including span 20) or fatty alcohol ethers (including Eumulgin B2) or poloxamer 124, Preferably, the cream-gels based on compounds of the avermectin family according to the invention comprise:
5 to 20% of oily phase,
0.25 to 1% of non-surfactant polymeric emulsifier,
0 to 2% of carbomer,
0 to 5% of co-emulsifier,
0.01 to 5% of at least one avermectin,
0.1 to 20% of solvents and/or propenetrating agents,
60 to 80% of water.

Preferably, the invermectin-based cream-gels according to the invention comprise:
5 to 20% of oily phase,
0.25 to 1% of non-surfactant polymeric emulsifier,
0 to 2% of carbomer,
0 to 5% of co-emulsifier,
0.01 to 5% of ivermectin,
0.1 to 20% of solvents and/or propenetrating agents,
60 to 80% of water.

More preferably, the invermectin-based cream-gels according to the invention comprise:
8 to 15% of oily phase,
0.25 to 1% of non-surfactant polymeric emulsifier,
0 to 2% of carbomer,
1 to 5% of co-emulsifier,
0.01 to 5% of ivermectin,
4 to 20% of solvent and/or propenetrating agents,
60 to 80% of water.

The compositions according to the invention may also contain additives normally employed in the cosmetics or pharmaceutical field, such as
humectants, such as glycerol or sorbitol;
gelling agents;
calmatives such as allantoin and talc;
preservatives such as para-hydroxybenzoic acid esters;
moisture regulators;
pH regulators such as citric acid and sodium hydroxide;
osmotic pressure modifiers;
UV-A and UV-B screening agents;
and anti-oxidants, such as α-tocopherol, butylhydroxyanisole (BHA) or butylhydroxytoluene (BHT), vitamin E, propyl gallate or citric acid.

Of course, those skilled in the art will be able to adapt the choice of additives or the optional compounds to be added to these compositions and also the procedure in such manner that the advantageous properties intrinsically associated with the present invention are not, or are not substantially, impaired by the envisaged addition.

These additives may be present in the composition at from 0.001 to 20% by weight relative to the total weight of the composition.

The cream-gels according to the invention will preferably have a viscosity corresponding to a flow threshold ranging from 15 to 60 Pascal (Pa), in particular from 20 to 50 Pa, measured using a Haake VT500-type rheometer.

The composition according to the invention can be prepared according to a "hot" (60-70° C.) or "cold" (ambient temperature) embodiment, according to the nature of the additives used.

According to one particular embodiment, the process for preparing the cream-gel according to the invention is carried out at ambient temperature (referred to as "cold") and comprises, successively, the following steps:

a) the constituents of the fatty phase are mixed until said phase is homogeneous;

b) the constituents of the aqueous phase are dissolved in water until complete homogeneity is obtained;

c) the non-surfactant polymeric emulsifier and the optional carbomer are dispersed in the aqueous phase obtained in b) until a homogeneous gel is obtained;

d) the fatty phase is incorporated, with moderate mechanical stirring, into the homogeneous gel obtained in c) so as to form an emulsion;

e) the constituents of active phase are mixed; the ivermectin is solubilized in this mixture; this phase is then incorporated into the emulsion obtained in d), with moderate mechanical stirring;

f) the neutralizing agent is incorporated at the end of step e) or during one of the preceding steps with moderate mechanical stirring so as to obtain a defined pH.

Preferably, this pH will be from 6.0 and 6.5, Verification of the natural pH of the mixture and optional correction with a solution of a neutralizing agent, and also incorporation of the optional additives, may be carried out, according to their chemical nature, during one of the steps of the preparation process described above.

The term "moderate mechanical stirring" used during the preparation process according to the invention is intended in particular to mean a mechanical stirring of from 500 and 1200 rpm measured with a Rayneri stirrer, and more preferably of from 600 and 1000 rpm.

The present invention also features formulating the compositions according to the invention into pharmaceutical preparations useful for treating dermatological conditions, disorders or afflictions.

The term "dermatological conditions" means more particularly rosacea, common acne, seborrhoeic dermatitis, perioral dermatitis, acneform eruptions, transient acantholytic dermatitis, and acne miliaris necrotica.

The compositions according to the invention are particularly suitable in a regime or regimen for the treatment of rosacea.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

| | |
|---|---|
| Ivermectin | 1.00 |
| Mineral oil | 10.00 |
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Phenoxyethanol | 1.00 |
| | qs pH |
| Sodium hydroxide | 6.30 |
| Purified water | qs 100 |

This cream-gel can be prepared according to the preparation process carried out at ambient temperature ("cold") comprising the following steps:

a) the mineral oil, the tocopherol and the propyl paraben are mixed until complete homogeneity is obtained;

b) the glycerol, the allantoin and the sodium edetate are dissolved in the water until complete homogeneity is obtained;

c) the acrylates/$C_{10-30}$ alkyl acrylate crosspolymer and the carbomer are dispersed in the aqueous phase previously obtained in step b), until a homogeneous gel is obtained;

d) the fatty phase obtained in step a) is incorporated, with moderate mechanical stirring (Rayneri: 1000 rpm), into the homogeneous gel obtained in step c);

e) the polysorbate 80; the propylene glycol and the phenoxyethanol are mixed; the ivermectin is solubilized in this mixture; this phase is then incorporated into the emulsion obtained in step d), with moderate mechanical stirring (Rayneri: approximately 600 rpm);

The neutralizing agent is incorporated, with moderate mechanical stirring (Rayneri: approximately 600 rpm), so as to obtain pH 6.30,

Example 2

| | |
|---|---|
| Ivermectin | 1.00 |
| Mineral oil | 10.00 |
| Tocopherol | 0.20 |
| Disodium edetate | 0.10 |
| Glycerol | 5.00 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Phenoxyethanol | 1.00 |
| | qs pH |
| Triethanolamine | 6.00 |
| Purified water | qs 100 |

Example 3

| | |
|---|---|
| Ivermectin | 0.50 |
| Capric/caprylic triglycerides | 10.00 |
| Tocopherol | 0.20 |
| Disodium edetate | 0.10 |
| Sorbitol | 5.00 |
| Zinc acetate | 0.50 |
| Acrylates/$C_{10-30}$ alkyl acrylate crosspolymer (PEMULEN TR1) | 0.30 |
| Carbomer | 0.15 |
| N-methylpyrrolidone | 5.00 |
| Phenoxyethanol | 1.00 |
| | qs pH |
| Sodium hydroxide | 6.00 |
| Purified water | qs 100 |

Example 4

| | |
|---|---|
| Ivermectin | 1.00 |
| Mineral oil | 10.00 |
| Sorbitan laurate | 1.00 |
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 3.00 |
| Poloxamer 124 | 1.00 |
| Propylene glycol | 4.00 |
| Phenoxyethanol | 1.00 |
| | qs pH 6.3 |
| Sodium hydroxide | 6.00 |
| Purified water | qs 100 |

Example 5

| | |
|---|---|
| Ivermectin | 1.00 |
| Mineral oil | 10.00 |
| Sorbitan laurate | 1.00 |

-continued

| | |
|---|---|
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Benzyl alcohol | 3.00 |
| | qs pH 6.3 |
| Sodium hydroxide | 6.00 |
| Purified water | qs 100 |

Example 6

| | |
|---|---|
| Ivermectin | 0.03 |
| Mineral oil | 10.00 |
| Sorbitan laurate | 1.00 |
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Benzyl alcohol | 3.00 |
| Poly(methyl methacrylate) | 2.00 |
| | qs pH 6.3 |
| Sodium hydroxide | 6.00 |
| Purified water | qs 100 |

Example 7

| | |
|---|---|
| Ivermectin | 0.03 |
| Mineral oil | 5.00 |
| Sweet almond oil | 5.00 |
| Sorbitan laurate | 1.00 |
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Benzyl alcohol | 3.00 |
| | qs pH 6.3 |
| Sodium hydroxide | 6.00 |
| Purified water | qs 100 |

Example 8

| | |
|---|---|
| Eprinomectin | 1.00 |
| Mineral oil | 10.00 |
| Tocopherol | 0.20 |
| Propyl paraben | 0.10 |
| Disodium edetate | 0.10 |
| Glycerol | 5.00 |
| Allantoin | 0.20 |
| Acrylates/$C_{10-30}$ alkyl acrylate crosspolymer (PEMULEN TR1) | 0.30 |
| Carbomer | 0.15 |
| Polysorbate 80 | 4.00 |
| Propylene glycol | 4.00 |
| Phenoxyethanol | 1.00 |
| | qs pH |
| Sodium hydroxide | 6.30 |
| Purified water | qs 100 |

These compositions are suited to be applied daily to a clean and dry skin. Patients suffering from rosacea note a relief from the first applications and an improvement in the rosacea blotches is observed from 10 days of treatment.

Example 9

Chemical and Physical Stability of the Formulations a) pH and Chemical Stability:

The variation in pH of the formulations is measured at 4, 8, 10 and 12 weeks at ambient temperature (25° C.) and at 45° C.

| Examples | Condition | Initial pH | pH week 4 | pH week 8 | pH week 10 | pH week 12 |
|---|---|---|---|---|---|---|
| 1 | 25° C./60% RH | 6.3 | 6.4 | 6.4 | 6.3 | 6.3 |
|   | 45° C./75% RH | 6.3 | 6.2 | 6.2 | 6.2 | 6.2 |
| 2 | 25° C./60% RH | 6.0 | 6.1 | 6.0 | 6.0 | 6.1 |
|   | 45° C./75% RH | 6.0 | 6.0 | 6.1 | 6.0 | 6.1 |

60% RH = 60% relative humidity
75% RH = 75% relative humidity

These results therefore show that the formulations described are stable over time with respect to pH, whether at ambient temperature or at 45° C.

The chemical stability is an assay of the active agent by HPLC at ambient temperature and 45° C., after 4, 8 and 12 weeks.

| Examples | Condition | Initial test | Test week 4 | Test week 8 | Test week 12 |
|---|---|---|---|---|---|
| 1 | 25° C./60% RH | 100.3 | 98.7 | 100.0 | 102.5 |
|   | 45° C./75% RH | 100.3 | 100.5 | 102.3 | 106.1 |
| 2 | 25° C./60% RH | 95.7 | 97.1 | 98.4 | 96.8 |
|   | 45° C./75% RH | 95.7 | 98.1 | 96.9 | 96.3 |

The results show that the active agent is stable in the composition and does not degrade over time whatever the temperature at which the product is stored.

b) Physical Stability:

The physical stability of the formulations is measured by microscopic and macroscopic observation of the formulation at ambient temperature, at 4° C. and at 45-55° C. after 4, 8, 10, 12 and 16 weeks.

At ambient temperature, the macroscopic observation makes it possible to guarantee the physical integrity of the products and the microscopic observation makes it possible to verify that there is no recrystallization of the solubilized active agent and no significant change in the size of the globules of the emulsion.

At 4° C., the microscopic observation verifies the non-recrystallization of the solubilized active agent.

At 45-55° C., the macroscopic observation verifies the integrity of the finished product.

The formulations described in examples 1 and 2 were tested. No recrystallization of the product nor any phenomenon of phase separation (dephasing) is observed over time, whether at ambient temperature, at 4° C. or at 45-55° C.

The formulations as described in the examples are therefore chemically and physically stable.

Example 10

Measurement of Viscosity of the Formulations

A Haake VT500-type rheometer with an SVDIN measuring sensor.

The rheograms were determined at 25° C. and at a shear rate of 4 s$^{-1}$ ($\gamma$), and by measuring the shear strain.

The term "flow threshold" ($\tau 0$ expressed in Pascals) means the force necessary (minimum shear strain) to overcome the Van der Waals-type cohesion forces and cause flow. The flow threshold is comparable to the value found at the shear rate of 4 s$^{-1}$.

These measurements are taken at T0 and after 4, 8 and 12 weeks.

| | Flow threshold ($\tau 0$ expressed in Pa) | | | |
|---|---|---|---|---|
| Example | T0 | 4 weeks | 8 weeks | 12 weeks |
| 1 | 20 | 20 | 46* | 44* |
| 2 | 26 | 26 | 22 | 23 |

*Use of a Haake VT 550 rheometer that induces a slight increase in the characteristic viscosity values.

The results obtained show no significant variation in the flow threshold; the viscosity of the composition according to the invention is therefore stable over time.

Example 11

Release-Penetration

A study was carried out in order to compare the release-penetration of ivermectin at 1% incorporated into compositions of the conventional emulsion (A) or cream-gel (example 1) type, applied non-occlusively to samples of human skin. The tritium-radio labeled compositions that were compared are a conventional emulsion formula A and example 1 in accordance with the invention.

Formula A (conventional emulsion) is as follows:

| Ingredients | % by weight relative to the total weight of the composition |
|---|---|
| Ivermectin | 1.00 |
| Glycerol | 4.0 |
| Steareth-2 | 1.0 |
| Steareth-21 | 2.0 |
| Aluminum magnesium silicate/titanium dioxide/silica | 1.0 |
| Methyl para-hydroxybenzoate | 0.2 |
| Propyl para-hydroxybenzoate | 0.1 |
| Disodium EDTA | 0.05 |

-continued

| Ingredients | % by weight relative to the total weight of the composition |
|---|---|
| Citric acid monohydrate | 0.05 |
| Isopropyl palmitate | 4.0 |
| Glyceryl/PEG 100 stearate | 2.0 |
| Self-emulsifiable wax | 1.0 |
| Palmitostearic acid | 2.00 |
| Dimethicone 200-350 cS | 0.5 |
| Propylene glycol | 4.0 |
| Glycerol triacetate | 1.00 |
| Phenoxyethanol | 0.5 |
| 10% sodium hydroxide | qs |
| Water | qs 100 |

The compositions are applied, for 16 hours, to the human skin samples placed on continuous-flow automatic diffusion cells (Scott/Dick, University of Newcastle-upon-Tyne, UK).

The radioactivity is then measured in the various layers of the skin and in the recipient liquid in contact with the skin sample.

| Composition | % total radioactivity recovered |
|---|---|
| Formula A | 2.10 |
| Example 1 | 3.28 |

The results obtained clearly show that the composition in the form of a cream-gel described in example 1 substantially and significantly increases the penetration of ivermectin into the various layers of the skin.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical/dermatological composition, said composition being a cream-gel comprising ivermectin and an oily phase dispersed in an aqueous phase by means of a non-surfactant polymeric emulsifier, said ivermectin being solubilized in a solvent and/or propenetrating agent selected from the group consisting of propylene glycol, ethanol, isopropanol, butanol, benzyl alcohol, N-methyl-2-pyrrolidone, DMSO, polysorbate 80, phenoxyethanol, and mixtures thereof, said non-surfactant polymeric emulsifier being an acrylate/$C_{10}$-$C_{30}$ alkyl acrylate crosspolymer, said non-surfactant polymeric emulsifier and a carbomer being dispersed in said aqueous phase, said composition further comprising a co-emulsifier selected from the group consisting of polysorbate 80, sorbitan laurate and poloxamer 124, said non-surfactant polymeric emulsifier and said co-emulsifier being the only emulsifiers in the composition, said oily phase amounting to 8 to 15% by weight of the composition, said oily phase comprising liquid oils having a melting point below 30° C. and having less than 0.1% by weight of waxes, fatty acids and fatty alcohols having a melting point above 30° C., that are in the solid state at ambient temperature, formulated into a topically applicable, physiologically acceptable medium therefor, said cream-gel having less than 0.1% by weight of waxes, fatty acids and fatty alcohols having a melting point above 30° C., that are in the solid state at ambient temperature, said cream-gel being physically and chemically stable for a period of 12 weeks.

2. The pharmaceutical/dermatological composition as defined by claim 1, said composition being a cream-gel comprising from 0.01% to 10% by weight of ivermectin.

3. The pharmaceutical/dermatological composition as defined by claim 1, said composition being a cream-gel comprising from 0.01% to 5% by weight of ivermectin.

4. The pharmaceutical/dermatological composition as defined by claim 1, said composition being a cream-gel comprising from 30% to 95% of water.

5. The pharmaceutical/dermatological composition as defined by claim 1, said composition being a cream-gel comprising:

| | |
|---|---|
| Ivermectin | 1.00% |
| Mineral oil | 10.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Phenoxyethanol | 1.00% |
| Sodium hydroxide | qs pH 6.30 |
| Purified water | qs 100; | said composition having less than 0.1% by weight of waxes, fatty acids and fatty alcohols having a melting point above 30° C., that are in the solid state at ambient temperature.

6. The pharmaceutical/dermatological composition as defined by claim 1, said composition being a cream-gel comprising:

| | |
|---|---|
| Ivermectin | 1.00% |
| Mineral oil | 10.00% |
| Tocopherol | 0.20% |
| Disodium edetate | 0.10% |
| Glycerol | 5.00% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Phenoxyethanol | 1.00% |
| Triethanolamine | qs pH 6.00 |
| Purified water | qs 100%; | said composition having less than 0.1% by weight of waxes, fatty acids and fatty alcohols having a melting point above 30° C., that are in the solid state at ambient temperature.

7. The pharmaceutical/dermatological composition as defined by claim 1, said composition being a cream-gel comprising:

| | |
|---|---|
| Ivermectin | 0.50% |
| Capric/caprylic triglycerides | 10.00% |
| Tocopherol | 0.20% |
| Disodium edetate | 0.10% |
| Sorbitol | 5.00% |
| Zinc acetate | 0.50% |
| Acrylates/$C_{10-30}$ alkyl acrylate crosspolymer (Pemulen TR1) | 0.30% |
| Carbomer | 0.15% |
| N-methylpyrrolidone | 5.00% |
| Phenoxyethanol | 1.00% |
| Sodium hydroxide | qs pH 6.00 |
| Purified water | qs 100%; | said composition having less than 0.1% by weight of waxes, fatty acids and fatty alcohols having a melting point above 30° C., that are in the solid state at ambient temperature.

8. The pharmaceutical/dermatological composition as defined by claim 1, said composition being a cream-gel comprising:

| | |
|---|---|
| Ivermectin | 1.00% |
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 3.00% |
| Poloxamer 124 | 1.00% |
| Propylene glycol | 4.00% |
| Phenoxyethanol | 1.00% |
| Sodium hydroxide | qs pH6.3 |
| Purified water | qs 100; | said composition having less than 0.1% by weight of waxes, fatty acids and fatty alcohols having a melting point above 30° C., that are in the solid state at ambient temperature.

9. A topically applicable pharmaceutical/dermatological composition, said composition being a cream-gel comprising:

| | |
|---|---|
| Ivermectin | 1.00% |
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Sodium hydroxide | qs pH6.3 |
| Purified water | qs 100; | said composition having less than 0.1% by weight of waxes, fatty acids and fatty alcohols having a melting point above 30° C., that are in the solid state at ambient temperature.

10. The pharmaceutical/dermatological composition as defined by claim 1, said composition being a cream-gel comprising:

| | |
|---|---|
| Ivermectin | 0.03% |
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |

-continued

| | |
|---|---|
| Allantoin | 0.20% |
| Acrylates/C$_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Poly(methyl methacrylate) | 2.00% |
| Sodium hydroxide | qs pH6.3 |
| Purified water | qs 100; | said composition having less than 0.1% by weight of waxes, fatty acids and fatty alcohols having a melting point above 30° C., that are in the solid state at ambient temperature.

11. The pharmaceutical/dermatological composition as defined by claim 1, said composition being a cream-gel comprising:

| | |
|---|---|
| Ivermectin | 0.03% |
| Mineral oil | 5.00% |
| Sweet almond oil | 5.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/C$_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Sodium hydroxide | qs pH 6.3 |
| Purified water | qs 100; | said composition having less than 0.1% by weight of waxes, fatty acids and fatty alcohols having a melting point above 30° C., that are in the solid state at ambient temperature.

12. A process for the formulation of the pharmaceutical/dermatological composition as defined by claim 1, comprising at ambient temperature:
a) mixing the constituents of the fatty phase until the resulting phase is homogeneous;
b) dissolving the constituents of the aqueous phase in water until homogeneity is obtained;
c) dispersing the polymeric emulsifier and an optional carbomer in the aqueous phase until a homogeneous gel is obtained;
d) incorporating the fatty phase, with moderate mechanical stirring, into the homogeneous gel obtained in c) to form an emulsion;
e) mixing the constituents of the active phase and solubilizing the ivermectin in the solvent and/or propenetrating agent; then incorporating this phase into the emulsion, with moderate mechanical stirring; and
f) incorporating a neutralizing agent, with moderate mechanical stirring, to obtain a defined pH.

13. A regime or regimen for the treatment of a dermatological condition, disorder or affliction which is selected from the group consisting of rosacea, common acne, seborrhoeic dermatitis, perioral dermatitis, acneform eruptions, transient acantholytic dermatitis, and acne miliaris necrotica, comprising topically applying onto the affected area of an individual in need of such treatment, a thus effective amount of a pharmaceutical/dermatological composition as defined by claim 1.

14. The pharmaceutical/dermatological composition as defined by claim 1, said composition being:

| (a) a cream-gel comprising: | |
|---|---|
| Ivermectin | 1.00% |
| Mineral oil | 10.00% |
| Tocopherol | 0.20% |
| Propyl paraben | 0.10% |
| Disodium edetate | 0.10% |
| Glycerol | 5.00% |
| Allantoin | 0.20% |
| Acrylates/C$_{10-30}$ alkyl acrylate crosspolymer (Pemulen TF1) | 0.30% |
| Carbomer | 0.15% |
| Polysorbate 80 | 4.00% |
| Propylene glycol | 4.00% |
| Phenoxyethanol | 1.00% |
| Sodium hydroxide | qs pH 6.30 |
| Purified water | qs 100; | said cream-gel having less than 0.1% by weight of waxes, fatty acids and fatty alcohols having a melting point above 30° C., that are in the solid state at ambient temperature;

| (b) a cream-gel comprising: | |
|---|---|
| Ivermectin | 1.00% |
| Mineral oil | 10.00% |
| Tocopherol | 0.20% |
| Disodium edetate | 0.10% |
| Glycerol | 5.00% |
| Acrylates/C$_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Phenoxyethanol | 1.00% |
| Triethanolamine | qs pH 6.00 |
| Purified water | qs 100%; | said cream-gel having less than 0.1% by weight of waxes, fatty acids and fatty alcohols having a melting point above 30° C., that are in the solid state at ambient temperature;

| (c) a cream-gel comprising: | |
|---|---|
| Ivermectin | 1.00% |
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/C$_{10-30}$ alkyl acrylate crosspolymer (Pemulen TR1) | 0.30% |
| Carbomer | 0.15% |
| Polysorbate 80 | 3.00% |
| Poloxamer 124 | 1.00% |
| Propylene glycol | 4.00% |
| Phenoxyethanol | 1.00% |
| Sodium hydroxide | qs pH 6.3 |
| Purified water | qs 100; | said cream-gel having less than 0.1% by weight of waxes, fatty adds and fatty alcohols having a melting point above 30° C., that are in the solid state at ambient temperature;

(d) a cream-gel comprising:

| Ivermectin | 1.00% |
|---|---|
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Sodium hydroxide | qs pH 6.3 |
| Purified water | qs 100; | said cream-gel having less than 0.1% by weight of waxes, fatty adds and fatty alcohols having a melting point above 30° C., that are in the solid state at ambient temperature;

(e) a cream-gel comprising:

| Ivermectin | 0.03% |
|---|---|
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Poly(methyl methacrylate) | 2.00% |
| Sodium hydroxide | qs pH 6.3 |
| Purified water | qs 100; | said cream-gel having less than 0.1% by weight of waxes, fatty acids and fatty alcohols having a melting point above 30° C., that are in the solid state at ambient temperature; or (f) a cream-gel comprising:

| Ivermectin | 0.03% |
|---|---|
| Mineral oil | 5.00% |
| Sweet almond oil | 5.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Sodium hydroxide | qs pH 6.3 |
| Purified water | qs 100; | said cream-gel having less than 0.1% by weight of waxes, fatty acids and fatty alcohols having a melting point above 30° C., that are in the solid state at ambient temperature.

15. The pharmaceutical/dermatological composition as defined by claim 1, said composition being:

(a) a cream-gel comprising:

| Ivermectin | 1.00% |
|---|---|
| Mineral oil | 10.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Phenoxyethanol | 1.00% |
| Sodium hydroxide | qs pH 6.30 |
| Purified water | qs 100; | said cream-gel having less than 0.1% by weight of waxes, fatty acids and fatty alcohols having a melting point above 30° C., that are in the solid state at ambient temperature;

(b) a cream-gel comprising:

| Ivermectin | 1.00% |
|---|---|
| Mineral oil | 10.00% |
| Tocopherol | 0.20% |
| Disodium edetate | 0.10% |
| Glycerol | 5.00% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Phenoxyethanol | 1.00% |
| Triethanolamine | qs pH 6.00 |
| Purified water | qs 100%; | said cream-gel having less than 0.1% by weight of waxes, fatty acids and fatty alcohols having a melting point above 30° C., that are in the solid state at ambient temperature;

(c) a cream-gel comprising:

| Ivermectin | 1.00% |
|---|---|
| Mineral oil | 10.00% |
| Sorbitan laurate | 1.00% |
| Tocopherol | 0.20% |
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 30 | 3.00% |
| Poloxamer 124 | 1.00% |
| Propylene glycol | 4.00% |
| Phenoxyethanol | 1.00% |
| Sodium hydroxide | qs pH 6.3 |
| Purified water | qs 100; | said cream-gel having less than 0.1% by weight of waxes, fatty acids and fatty alcohols having a melting point above 30° C., that are in the solid state at ambient temperature; or (d) a cream-gel comprising:

| Ivermectin | 1.00% |
|---|---|
| Mineral oil | 10.00% |
| Sorbitan laurate | 1.00% |
| Tocopherol | 0.20% |

-continued

| (d) a cream-gel comprising: | |
|---|---|
| Propyl paraben | 0.10% |
| Disodium edetate | 0.10% |
| Glycerol | 5.00% |
| Allantoin | 0.20% |
| Acrylates/$C_{10-30}$ alkyl acrylate crosspolymer (Pemulen TR1) | 0.30% |
| Carbomer | 0.15% |
| Polysorbate 80 | 4.00% |
| Propylene glycol | 4.00% |
| Benzyl alcohol | 3.00% |
| Sodium hydroxide | qs pH 6.3 |
| Purified water | qs 100; | said cream-gel having less than 0.1% by weight of waxes, fatty acids and fatty alcohols having a melting point above 30° C., that are in the solid state at ambient temperature.

16. A regime or regimen for the treatment of a dermatological condition, disorder or affliction which is selected from the group consisting of rosacea, common acne, seborrhoeic dermatitis, perioral dermatitis, acneform eruptions, transient acantholytic dermatitis, and acne miliaris necrotica, comprising topically applying onto the affected area of an individual in need of such treatment, a thus effective amount of a pharmaceutical/dermatological composition as defined by claim 14.

17. A regime or regimen for the treatment of a dermatological condition, disorder or affliction which is selected from the group consisting of rosacea, common acne, seborrhoeic dermatitis, perioral dermatitis, acneform eruptions, transient acantholytic dermatitis, and acne miliaris necrotica, comprising topically applying onto the affected area of an individual in need of such treatment, a thus effective amount of a pharmaceutical/dermatological composition as defined by claim 15.

18. A regime or regimen for the treatment of a dermatological condition, disorder or affliction which is selected from the group consisting of rosacea, common acne, seborrhoeic dermatitis, perioral dermatitis, acneform eruptions, transient acantholytic dermatitis, and acne miliaris necrotica, comprising topically applying onto the affected area of an individual in need of such treatment, a thus effective amount of a pharmaceutical/dermatological composition as defined by claim 9.

19. A regime or regimen for the treatment of rosacea, comprising topically applying onto the affected skin area of an individual in need of such treatment, a thus effective amount of the pharmaceutical/dermatological composition as defined by claim 1.

20. A regime or regimen for the treatment of rosacea, comprising topically applying onto the affected skin area of an individual in need of such treatment, a thus effective amount of the pharmaceutical/dermatological composition as defined by claim 14.

21. A regime or regimen for the treatment of rosacea, comprising topically applying onto the affected skin area of an individual in need of such treatment, a thus effective amount of the pharmaceutical/dermatological composition as defined by claim 15.

22. A regime or regimen for the treatment of rosacea, comprising topically applying onto the affected skin area of an individual in need of such treatment, a thus effective amount of the pharmaceutical/dermatological composition as defined by claim 5.

23. A regime or regimen for the treatment of rosacea, comprising topically applying onto the affected skin area of an individual in need of such treatment, a thus effective amount of the pharmaceutical/dermatological composition as defined by claim 6.

24. A regime or regimen for the treatment of rosacea, comprising topically applying onto the affected skin area of an individual in need of such treatment, a thus effective amount of the pharmaceutical/dermatological composition as defined by claim 7.

25. A regime or regimen for the treatment of rosacea, comprising topically applying onto the affected skin area of an individual in need of such treatment, a thus effective amount of the pharmaceutical/dermatological composition as defined by claim 8.

26. A regime or regimen for the treatment of rosacea, comprising topically applying onto the affected skin area of an individual in need of such treatment, a thus effective amount of the pharmaceutical/dermatological composition as defined by claim 9.

27. A regime or regimen for the treatment of rosacea, comprising topically applying onto the affected skin area of an individual in need of such treatment, a thus effective amount of the pharmaceutical/dermatological composition as defined by claim 10.

28. A regime or regimen for the treatment of rosacea, comprising topically applying onto the affected skin area of an individual in need of such treatment, a thus effective amount of the pharmaceutical/dermatological composition as defined by claim 11.

* * * * *